United States Patent
Zuo et al.

(10) Patent No.: US 12,188,919 B2
(45) Date of Patent: Jan. 7, 2025

(54) METHOD AND SYSTEM FOR MEASURING COMPOSITION AND PROPERTY OF FORMATION FLUID

(71) Applicants: CHINA OILFIELD SERVICES LIMITED, Tianjin (CN); CHINA NATIONAL OFFSHORE OIL CORPORATION, Beijing (CN)

(72) Inventors: Youxiang Zuo, Hebei (CN); Yongren Feng, Hebei (CN); Tao Lu, Hebei (CN); Sun Kong, Hebei (CN); Yang Shen, Hebei (CN); Xiaofei Qin, Hebei (CN); Xiaodong Chu, Hebei (CN); Yongchao Chen, Hebei (CN); Xingfang Wu, Hebei (CN); Lin Huang, Hebei (CN)

(73) Assignees: CHINA OILFIELD SERVICES LIMITED, Tianjin (CN); CHINA NATIONAL OFFSHORE OIL CORPORATION, Beijing (CN)

( * ) Notice: Subject to any disclaimer, the term of this patent is extended or adjusted under 35 U.S.C. 154(b) by 699 days.

(21) Appl. No.: 17/433,519

(22) PCT Filed: Feb. 5, 2020

(86) PCT No.: PCT/CN2020/074353
§ 371 (c)(1),
(2) Date: Aug. 24, 2021

(87) PCT Pub. No.: WO2020/215850
PCT Pub. Date: Oct. 29, 2020

(65) Prior Publication Data
US 2022/0155275 A1    May 19, 2022

(30) Foreign Application Priority Data
Apr. 25, 2019    (CN) ......................... 201910341093.7

(51) Int. Cl.
*G01N 33/28* (2006.01)
*E21B 49/08* (2006.01)
(Continued)

(52) U.S. Cl.
CPC ..... *G01N 33/2823* (2013.01); *E21B 49/0875* (2020.05); *G01N 30/8693* (2013.01);
(Continued)

(58) Field of Classification Search
CPC ............. E21B 49/0875; E21B 2200/20; E21B 2200/22; E21B 49/081; E21B 49/086;
(Continued)

(56) References Cited

U.S. PATENT DOCUMENTS 7,966,273 B2    6/2011    Hegeman et al.
9,121,959 B2 *  9/2015    Zhang ...................... G01V 5/08
(Continued)

FOREIGN PATENT DOCUMENTS

CN    1693893 A    11/2005
CN    101182769 A    5/2008
(Continued)

OTHER PUBLICATIONS

International Search Report and Written Opinion for Application No. PCT/CN2020/074353, dated Apr. 30, 2020, 6 Pages (including English Translation).
(Continued)

*Primary Examiner* — Elias Desta
(74) *Attorney, Agent, or Firm* — Brooks Kushman, P.C.

(57) ABSTRACT

Provided are a method and system for measuring a composition and property of a formation fluid. The method includes: acquiring a measuring model used for measuring a composition and a property of a formation fluid; using a signal measured by a sensor on a downhole hydrocarbon formation tester in real-time as input data and inputting the input data into the measuring model; processing the input data by the measuring model; and directly outputting a processing result as data on the composition and the property of the real-time formation fluid, or parsing the data on
(Continued)

the composition and the property of the real-time formation fluid according to the processing result.

17 Claims, 11 Drawing Sheets

(51) Int. Cl.
    *G01N 30/86*      (2006.01)
    *G06N 20/00*      (2019.01)
    *G01N 30/02*      (2006.01)

(52) U.S. Cl.
    CPC ............ *G06N 20/00* (2019.01); *E21B 49/081* (2013.01); *E21B 49/086* (2013.01); *E21B 2200/20* (2020.05); *E21B 2200/22* (2020.05); *G01N 2030/025* (2013.01)

(58) Field of Classification Search
    CPC ........... G01N 33/2823; G01N 30/8693; G01N 2030/025; G06N 20/00
    See application file for complete search history.

(56) References Cited

U.S. PATENT DOCUMENTS

| | | | |
|---|---|---|---|
| 9,460,408 | B2 | 10/2016 | Berlandier et al. |
| 11,371,345 | B2 * | 6/2022 | Olapade .................. E21B 49/08 |
| 11,441,422 | B2 * | 9/2022 | Kristensen .............. E21B 49/10 |
| 2005/0242807 | A1 | 11/2005 | Freedman |
| 2007/0143023 | A1 | 6/2007 | Betancourt et al. |
| 2011/0119212 | A1 | 5/2011 | De Bruin et al. |

FOREIGN PATENT DOCUMENTS

| | | |
|---|---|---|
| CN | 101498215 A | 8/2009 |
| CN | 102339326 A | 2/2012 |
| CN | 106570524 A | 4/2017 |
| CN | 108533254 A | 9/2018 |
| CN | 108573320 A | 9/2018 |
| CN | 108596251 A | 9/2018 |
| CN | 108875122 A | 11/2018 |
| CN | 109446735 A | 3/2019 |
| CN | 110056348 A | 7/2019 |
| EP | 2245568 A4 | 12/2012 |
| WO | 2010120285 A1 | 10/2010 |

OTHER PUBLICATIONS

First Office Action for Chinese Application No. 201910341093.7, dated Apr. 26, 2020, 22 Pages (including English Translation).
Second Office Action for Chinese Application No. 201910341093.7, dated Jul. 30, 2020, 16 Pages (including English Translation).
Third Office Action for Chinese Application No. 201910341093.7, dated Oct. 21, 2020, 17 Pages (including English Translation).

* cited by examiner

METHOD AND SYSTEM FOR MEASURING COMPOSITION AND PROPERTY OF FORMATION FLUID

CROSS-REFERENCE TO RELATED APPLICATION

This application is the U.S. national phase of PCT Application No. PCT/CN2020/074353 filed on Feb. 5, 2020, which claims priority to Chinese Patent Application No. 201910341093.7 filed on Apr. 25, 2019, both of which are hereby incorporated herein by reference in their entireties.

TECHNICAL FIELD

Embodiments of the present application relate to, but are not limited to, logging (formation testing and fluid sampling) technology, in particular to a method and a system for measuring a composition and a property of a formation fluid.

BACKGROUND

In recent years, downhole fluid identification technology has made great progress especially in the aspect of hardware. However, the efficiency and accuracy still need to be improved in terms of real-time analysis of downhole fluids and sampling of undisturbed formation fluids, and particularly in real-time analysis of downhole spectra used for obtaining the composition and property of downhole fluid components (such as oil, gas, water phase fractions, gas-oil ratio, mud filtrate contamination, real-time sampling guidance).

SUMMARY

The following is a summary of the subject matter described in detail herein. This summary is not intended to limit the protection scope of the claims.

Embodiments of the present application provide a method and a system for measuring a composition and a property of a formation fluid, which can quickly and accurately measure the composition and property of the formation fluid and improve logging efficiency and accuracy.

In an aspect, an embodiment of the present application provides a method for measuring a composition and a property of a formation fluid, which may include:

acquiring a measuring model used for measuring a composition and a property of a formation fluid;

using a signal measured by a sensor on a downhole hydrocarbon formation tester in real-time as input data and inputting the input data into the measuring model;

processing the input data by the measuring model; and directly outputting a processing result as data on the composition and the property of the real-time formation fluid, or parsing the data on the composition and the property of the real-time formation fluid according to the processing result.

In an exemplary embodiment, the measuring model is obtained by training pre-created machine learning models based on big data about compositions and properties of various reservoir fluids and measurement signals of downhole sensors as sample data sets.

In an exemplary embodiment, acquiring the measuring model used for measuring the composition and the property of the formation fluid may include: retrieving a pre-created and pre-trained measuring model, or creating and training the measuring model in real-time.

In an exemplary embodiment, before using the signal measured by the sensor on the downhole hydrocarbon formation tester in real-time as the input data of the measuring model and inputting the input data into the measuring model, the method further includes:

loading the pre-trained measuring model into the downhole hydrocarbon formation tester to input the signal measured by the sensor on the downhole hydrocarbon formation tester in real-time into the measuring model during a real-time logging process of the downhole hydrocarbon formation tester.

In an exemplary embodiment, creating and training the measuring model may include:

establishing a database about compositions and properties of various reservoir fluids and the measurement signals of downhole sensors;

extracting the sample data set from the database, and training the pre-created machine learning models by the sample data set; and acquiring an optimal machine learning model from trained machine learning models as the measuring model.

In an exemplary embodiment, establishing the database about the compositions and the properties of various reservoir fluids and the measurement signals of the downhole sensors may include:

acquiring single-phase reservoir fluid samples meeting a preset requirement in one or more of the following manners: surface sampling and downhole sampling; the single-phase reservoir fluid samples may include oil phase reservoir fluid samples, gas phase reservoir fluid samples and water phase reservoir fluid samples;

performing single-stage flash on the single-phase reservoir fluid sample at standard atmospheric pressure and room temperature to separate equilibrium flashed gas and liquid; performing gas chromatography analysis on the flashed gas and the flashed liquid respectively to obtain a composition and a first property of the single-phase reservoir fluid sample by use of mass balance calculations; performing a fluid pressure volume temperature (PVT) test on the single-phase reservoir fluid sample under a first preset pressure and a first preset temperature to obtain a second property of the single-phase reservoir fluid sample; wherein the first preset pressure is greater than the standard atmospheric pressure and the first preset temperature is greater than the room temperature; and adding data related to the composition, the first property and the second property of the single-phase reservoir fluid sample as a part of big data of the formation fluid into the database.

In an exemplary embodiment, the first property may include any one or more of the following: gas-oil ratio, American Petroleum Institute (API) gravity, molecular weight, sulfur content, carbon content, hydrogen content, Watson K value, SARA content and paraffin content; wherein SARA refers to saturated hydrocarbon, aromatic hydrocarbon, resin and asphaltene; and the second property may include any one or more of the following: bubble point, dew point, constant composition expansion (CCE) test characteristics, differential liberation (DL) test characteristics, constant volume depletion (CVD) test characteristics, separator test characteristics, density, viscosity, conductivity, compressibility, formation volume factor, paraffin wax formation condition and asphaltene onset condition.

In an exemplary embodiment, the method may further include
performing any one or more of the following:
measuring the volume, temperature and pressure of the flashed gas when the gas chromatography analysis is performed on the flashed gas and added into the database;
measuring volume, temperature, pressure, density and molecular weight of the flashed liquid when the gas chromatography analysis is performed on the flashed liquid and adding the volume, the temperature, the pressure, the density and the molecular weight of the flashed liquid into the database;
performing any one or more of the following measurements on the single-phase reservoir fluid sample under the first preset pressure and the first preset temperature: continuous near-infrared spectrum, nuclear magnetic resonance (NMR), acoustic wave, fluorescence and dielectric constant measurement, and results of the measurements are added into the database.

In an exemplary embodiment, the method may further include: adding different drilling mud filtrates into different single-phase reservoir fluid samples, and performing the PVT test on the single-phase reservoir fluid samples in which corresponding drilling mud filtrates are added; in addition, mixing oil and water, and measuring oil water content, continuous near-infrared spectrum, nuclear magnetic resonance (NMR), acoustic wave, fluorescence and dielectric constant measurement, and adding the results of measurement into the database.

In an exemplary embodiment, extracting the sample data set from the database, and training the pre-created machine learning models by the sample data set may include:
preprocessing and standardizing the sample data set, wherein the preprocessing may include any one or more of the following: denoising, outlier removal and smoothing;
dividing the preprocessed and standardized sample data set into a first data set and a second data set;
training each of the machine learning models using one of preset machine learning methods based on the first data set and the second data set, and obtaining an optimal trained machine learning model among all the trained models as the measuring model;
wherein the first data set serves as an input data vector/matrix of the machine learning model, and the second data set serves as a target data vector/matrix of an output data vector/matrix of the machine learning model.

Herein, the input data vector/matrix and the target data vector/matrix may be one-dimensional or multi-dimensional.

In an exemplary embodiment, the preset machine learning method may include a supervised machine learning method;
training each of the machine learning models using the preset machine learning methods based on the first data set and the second data set, and obtaining the optimal machine learning model among all the trained models as the measuring model may include:
performing following operations respectively on each function in a predefined function set: inputting a standardized first data set into each untrained machine learning model; calculating the output data vector/matrix according to the first data set and a function currently loaded in the machine learning model;
comparing multiple calculated output data vectors/matrix with the target data vectors/matrix respectively, and determining a first function corresponding to the first output data vector/matrix with the smallest deviation with respect to the target data vector/matrix and a current coefficient of the first function from target data vectors/matrix in the multiple comparison results; and
using a machine learning model loaded with the first function as an optimal trained machine learning model, wherein the loaded first function has the current coefficient.

In an exemplary embodiment, the method may further include: supplementing an output data vector/matrix whose deviation with respect to the target data vector/matrix meets a preset deviation threshold to the database in one or more of following processes: during a training process of the machine learning models and an implementation process of measuring the composition and the property of the formation fluid.

In another aspect, an embodiment of the present application further provides a system for measuring composition and property of formation fluid, which may include a processor and a computer readable storage medium, wherein instructions are stored in the computer readable storage medium, and the processor is configured to execute the instructions to perform the method for measuring composition and property of formation fluid according to any one of the aforementioned embodiments.

Other aspects will become apparent after reading and understanding the brief description of the drawings and the embodiments of the present application.

BRIEF DESCRIPTION OF DRAWINGS

Accompanying drawings are used to provide a further understanding of solutions of embodiments of the present application, constitute a part of the specification to explain the technical solutions together with the embodiments of the present application, and do not constitute limitations on the technical solutions.

DETAILED DESCRIPTION

Hereinafter, embodiments of the present application will be described with reference to the accompanying drawings. The embodiments in the present application and the features in the embodiments may be combined with each other randomly if there is no conflict.

The steps shown in a flowchart of the drawings may be performed in a computer system such as a set of computer executable instructions. Moreover, although a logical order is shown in the flowchart, in some cases, the steps shown or described may be performed in a different order from that here.

Figure 1:
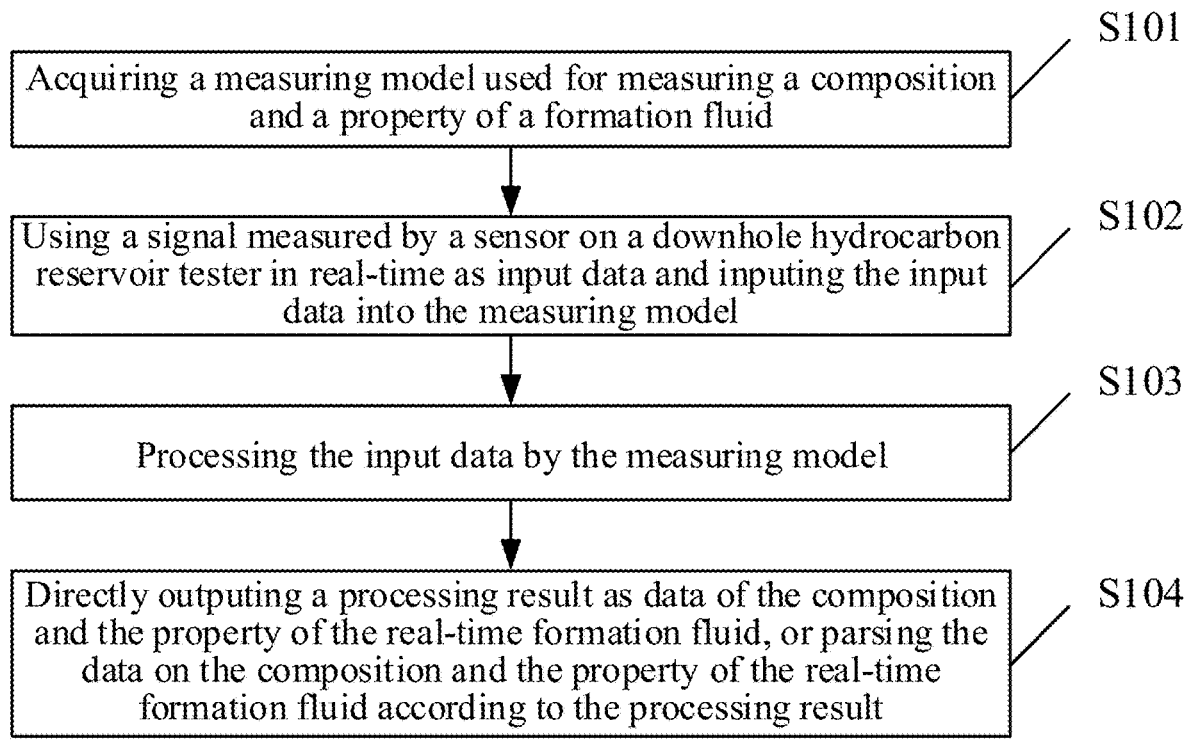
FIG. 1 is a flowchart of a method for measuring a composition and a property of a formation fluid according to an embodiment of the present application.

An embodiment of the present application provides a method for measuring a composition and a property of a formation fluid, as shown in FIG. 1, the method may include steps S101-S104:

S101, acquiring a measuring model used for measuring a composition and a property of a formation fluid;

S102, using a signal measured by a sensor on a downhole hydrocarbon formation tester in real-time as input data and inputting the input data into the measuring model;

S103, processing the input data by the measuring model; and

S104, directly outputting a processing result as data of the composition and the property of the real-time formation fluid, or explaining or predicting the data on the composition and property of the real-time formation fluid according to the processing result.

In an exemplary embodiment, the measuring model is obtained by training the pre-created machine learning models by using big data about compositions and properties of various reservoir fluids and measurement signals of downhole sensors as sample data sets.

In an exemplary embodiment, the step of acquiring the measuring model used for measuring the composition and the property of the formation fluid may include: retrieving a pre-created and pre-trained measuring model, or creating and training the measuring model in real-time.

Figure 2:
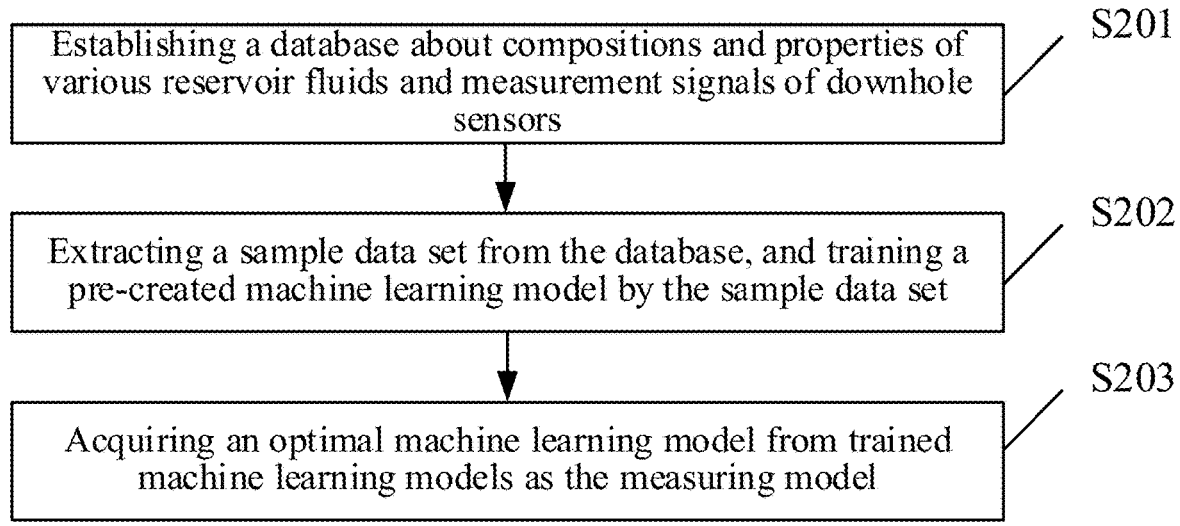
FIG. 2 is a flowchart of a method for creating and training a measuring model according to an embodiment of the present application.

In an exemplary embodiment, as shown in FIG. 2, the step of creating and training the measuring model may include steps S201-S203.

S201, establishing a database about compositions and properties of various reservoir fluids and measurement signals of downhole sensors;

S202, extracting the sample data set from the database, and training multiple pre-created machine learning models by the sample data set; and S203, acquiring an optimal machine learning model from trained machine learning models as the measuring model.

In an exemplary embodiment, the database may be a large database or a very large database.

In an exemplary embodiment, data on compositions and properties of a variety of reservoir fluids may be measured by using various surface and downhole measurement means, and a database containing the data on the compositions (such as $CO_2$, $C_1$, $C_2$, $C_3$, ..., $C_{29}$, $C_{30+}$), properties and sensor measurement signals of the reservoir fluids (such as gas, condensate gas, oil, water, oil-based mud filtrate, water-based mud filtrate, etc.) may be established.

Figure 3:
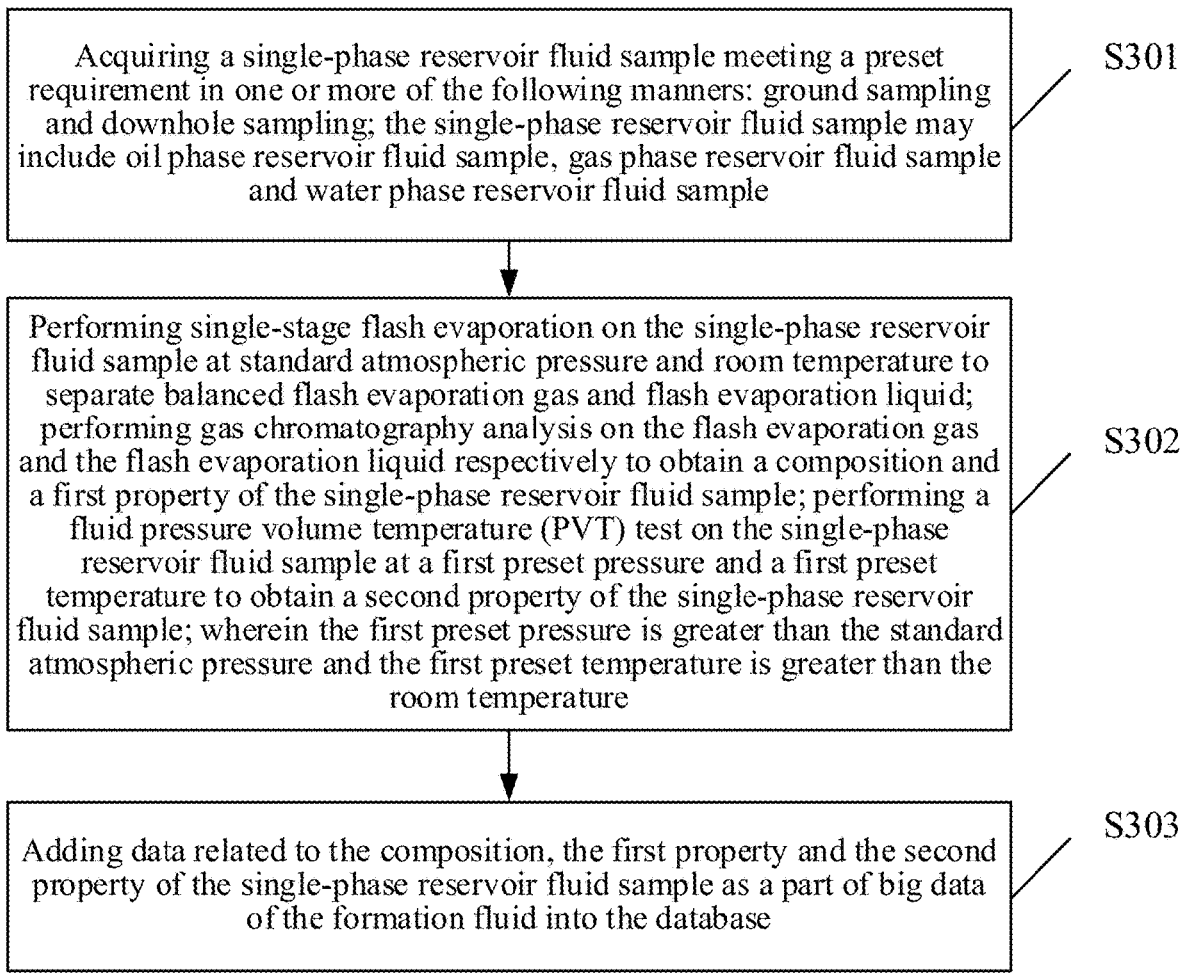
FIG. 3 is a flowchart of a method for establishing a database about compositions and properties of various reservoir fluids and measurement signals of downhole sensors according to an embodiment of the present application.

In an exemplary embodiment, as shown in FIG. 3, the step of establishing the database about the compositions and the properties of the various reservoir fluids and the measurement signals of the downhole sensors may include steps S301-S303:

S301, acquiring a single-phase reservoir fluid sample meeting a preset requirement in one or more of the following manners: surface sampling and downhole sampling; wherein the single-phase reservoir fluid sample may include oil phase reservoir fluid sample, gas phase reservoir fluid sample and water phase reservoir fluid sample.

In an exemplary embodiment, representative reservoir fluid samples (such as meeting preset requirements) may be obtained first. The sampling methods for reservoir fluids include the following two: surface sampling and downhole sampling. Operating conditions of a surface separator may be kept stable when the surface sampling is adopted. The oil and gas separated by the surface separator may be collected, and related parameters such as gas-oil ratio may be recorded, so that the collected oil and gas from the surface separator may be matched in laboratory according to the obtained gas-oil ratio and other related parameters, so as to generate a representative single-phase reservoir fluid sample. If the downhole sampling is adopted, it may be checked in the laboratory whether a sample collected downhole is a representative single-phase reservoir fluid sample.

S302, performing single-stage flash on the single-phase reservoir fluid sample at standard atmospheric pressure and room temperature to separate equilibrium flashed gas and liquid; performing gas chromatography analysis on the flashed gas and the flashed liquid respectively to obtain a composition and a first property of the single-phase reservoir fluid sample by use of mass balance calculations; performing a fluid pressure volume temperature (PVT) test on the single-phase reservoir fluid sample at a first preset pressure and a first preset temperature to obtain a second property of the single-phase reservoir fluid sample; wherein the first preset pressure is greater than the standard atmospheric pressure and the first preset temperature is greater than the room temperature.

S303, adding data related to the composition, the first property and the second property of the single-phase reservoir fluid sample as a part of big data of the formation fluid into the database.

In an exemplary embodiment, the method may further include
performing any one or more of the following:
measuring volume, temperature and pressure of the flashed gas when the gas chromatography analysis is performed on the flashed gas, and adding the volume, the temperature and the pressure into the database;
measuring volume, temperature, pressure, density and molecular weight of the flashed liquid when the gas chromatography analysis is performed on the flashed liquid and adding the volume, the temperature, the pressure, the density and the molecular weight into the database;
performing any one or more of the following measurements on the single-phase reservoir fluid sample at the first preset pressure and the first preset temperature: continuous near-infrared spectrum, nuclear magnetic resonance (NMR), acoustic wave, fluorescence and dielectric constant measurement, and adding the measurement results into the database.

In an exemplary embodiment, the first property may include but is not limited to any one or more of the following: gas-oil ratio, API (American Petroleum Institute) gravity, molecular weight, sulfur content, carbon content, hydrogen content, Watson K value, SARA content and paraffin content; wherein SARA refers to saturated hydrocarbon, aromatic hydrocarbon, resin and asphaltene.

In an exemplary embodiment, the second property may include, but is not limited to, any one or more of the following: bubble point, dew point, constant composition expansion (CCE) test characteristics, differential liberation (DL) test characteristics, constant volume depletion (CVD) test characteristics, separator test characteristics, density, viscosity, conductivity, compressibility coefficient, formation volume factor, paraffin wax formation condition and asphaltene onset condition.

In an exemplary embodiment, a single-stage flash is performed on a representative single-phase reservoir fluid sample to separate the equilibrium flashed gas and liquid at atmospheric pressure (such as standard atmospheric pressure) and the room temperature. Gas chromatography analysis is performed on the flashed gas, and volume, temperature and pressure of the flashed gas are measured. In addition, gas chromatography analysis may be performed on the flashed liquid, density and molecular weight of the flashed liquid may be measured, and SARA (wherein SARA refers to saturated hydrocarbon, aromatic hydrocarbon, resin and asphaltene) content analysis and paraffin content analysis may be performed. According to the measured related parameters and a material balance equation during the single-stage flash, composition, gas-oil ratio, API gravity, molecular weight, sulfur content, carbon content, hydrogen content, Watson K value, SARA content and paraffin content of the representative single-phase reservoir fluid sample are obtained.

In an exemplary embodiment, under high temperature and high pressure (such as a first preset pressure and a first preset temperature), a fluid PVT (pressure volume temperature) test may be performed on a representative single-phase reservoir fluid sample to obtain any one or more of the following fluid properties: bubble point, dew point, CCE test, DL test, CVD test, separator test, density, viscosity, conductivity, compressibility coefficient, FVF (formation volume factor), paraffin wax formation condition, and asphaltene onset condition, etc. In addition, the representative single-phase reservoir fluid sample may be measured by continuous near-infrared spectrum, NMR, acoustic wave, fluorescence and dielectric constant, etc. under high temperature and high pressure.

In an exemplary embodiment, the continuous near-infrared spectrum, NMR, acoustic wave, fluorescence, dielectric constant and PVT data of corresponding reservoir fluid samples which are measured during downhole real-time operation and change with time and pumped volume may include component composition, gas-oil ratio, API gravity, molecular weight, sulfur content, carbon content, hydrogen content, Watson K value, SARA content, paraffin content, bubble point, dew point, CCE, DL, CVD, separator, density, viscosity, conductivity, compressibility coefficient, formation volume factor, paraffin wax formation condition, asphaltene onset condition, etc.

In an exemplary embodiment, analysis on gas-water ratio and ion concentration may be performed on a water sample. In addition, measurements of continuous near-infrared spectrum, NMR, acoustic wave, fluorescence, dielectric constant, pH value, etc. may be performed under high temperature and high pressure.

In an exemplary embodiment, all the parameters and data measured in step S302 may be added into the database.

In an exemplary embodiment, the method may further include adding different drilling mud filtrates to different single-phase reservoir fluid samples, and performing the PVT test on the single-phase reservoir fluid samples into which corresponding drilling mud filtrates are added.

In an exemplary embodiment, the method may further include mixing oil and water, and measuring oil water content, continuous near-infrared spectrum, nuclear magnetic resonance (NMR), acoustic wave, fluorescence and dielectric constant measurement, and adding the measurement results into the database.

In an exemplary embodiment, considering the influence of different drilling mud (water-based and oil-based) filtrates on fluids, various drilling mud filtrates may be added to different reservoir fluid samples (such as water samples, oil samples and gas samples), and PVT tests may be performed on the reservoir fluid samples into which drilling mud filtrates are added to measure the component compositions, mud filtrate contamination, molecular weights, gas-oil ratios, API gravities, molecular weights, sulfur contents, carbon contents, hydrogen contents, Watson K values, bubble points, dew points, CCEs, DLs, CVDs, separators, densities, viscosities, compressibility coefficients, formation volume factors, gas-water ratios, etc. of the reservoir fluid samples and ion composition analysis may be performed. In addition, measurements of continuous near-infrared spectrum, NMR, acoustic wave, fluorescence, dielectric constant and pH value may be performed under high temperature and high pressure. Various measurement results are added into the database to enrich the data of the database.

In an exemplary embodiment, considering determination of downhole oil-water rate, different proportions of oil and water may be mixed into different reservoir fluid samples (such as water samples, oil samples and gas samples), and measurements of continuous near-infrared spectrum, NMR, acoustic wave, fluorescence, dielectric constant and so on may be performed at normal temperature and pressure and high temperature and high pressure on the reservoir fluid samples mixed with corresponding proportions of gas, oil and water. In addition, PVT test is performed on the reservoir fluid samples mixed with corresponding proportions of gas, oil and water to measure the component compositions, mud filtrate contamination, molecular weights, gas-oil ratios, API gravities, molecular weights, sulfur contents, carbon contents, hydrogen contents, Watson K values, bubble points, dew points, CCEs, DLs, CVDs, separators, densities, viscosities, compressibility coefficients, formation volume factors, gas-water ratios, etc. of the reservoir fluid samples and ion composition analysis may be performed thereon. Finally, the measurement results may be added into the database to enrich the data of the database.

In an exemplary embodiment, according to a large number of different reservoir characteristic parameters, different reservoir fluid property parameters and different logging tool geometric parameters, a large quantity of result data are obtained by CFD (computational fluid dynamics) and reservoir simulator simulation, and the result data may be added to the database.

In an exemplary embodiment, the downhole real-time and laboratory measurement data (and other data), including but not limited to the above, may be stored in a relational database (such as SQL database) and/or a non-relational database (such as NoSQL database) to form a database of in-house wireline and hydrocarbon formation test while drilling.

Figure 4:
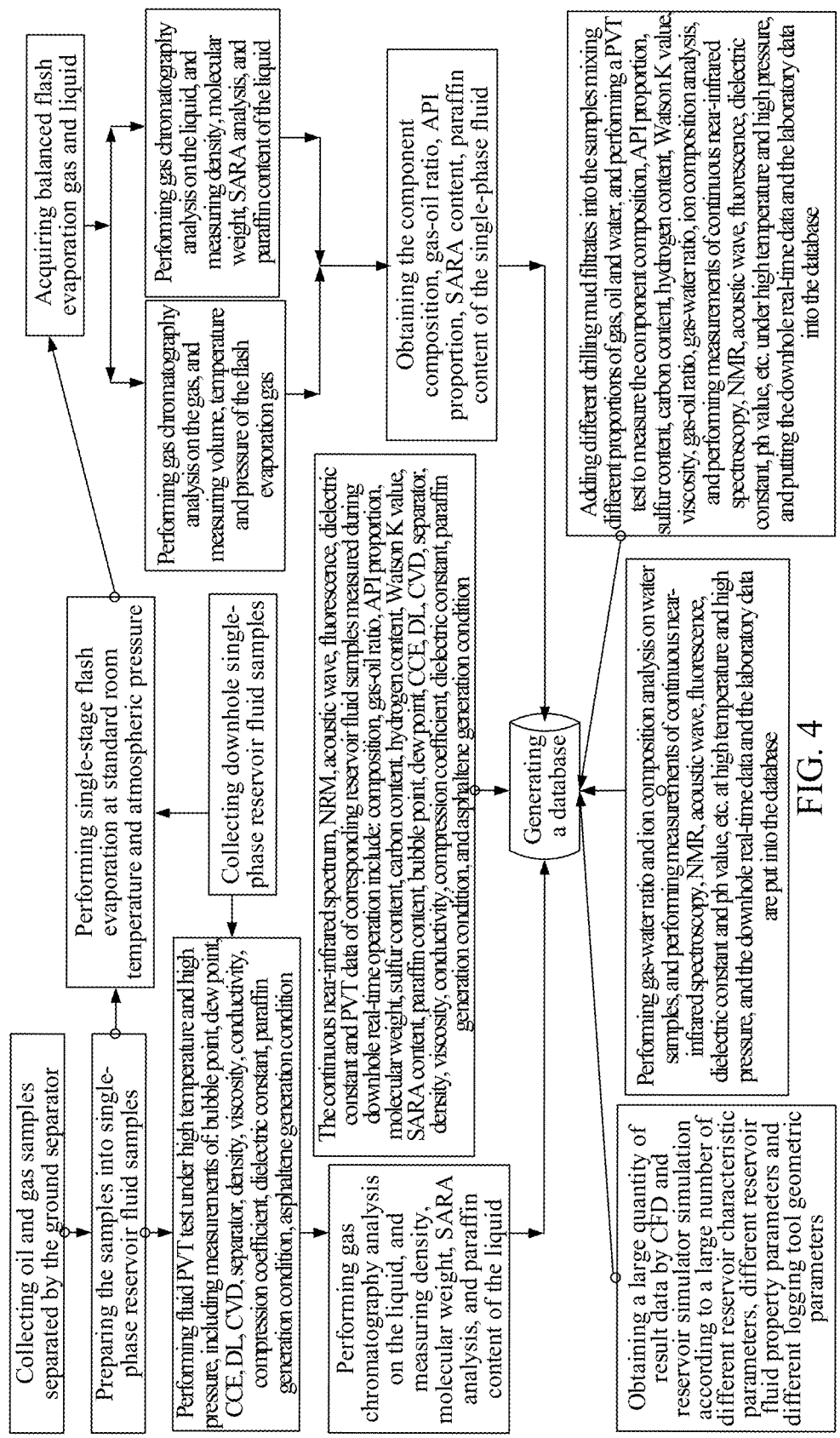
FIG. 4 is a schematic diagram of a method for establishing a database about compositions and properties of various reservoir fluids and measurement signals of downhole sensors according to an embodiment of the present application.

In an exemplary embodiment, as shown in FIG. 4, the method for establishing a database includes the following steps:

collecting oil and gas samples separated by a surface separator, and preparing the samples into a single-phase reservoir fluid sample; and collecting a downhole single-phase reservoir fluid sample.

In an aspect, single-stage flash is performed on the single-phase reservoir fluid sample at standard atmospheric pressure and the room temperature to obtain equilibrium flashed gas and liquid;

gas chromatography analysis is performed on the gas, and volume, temperature and pressure of the flashed gas are measured, and gas chromatography analysis is performed on the flashed liquid, and density, molecular weight, sulfur content, carbon content, hydrogen content, Watson K value of the flashed liquid are measured, and SARA (wherein SARA refers to saturated hydrocarbon, aromatic hydrocarbon, resin and asphaltene) content analysis and paraffin content analysis are performed. The composition content, gas-oil ratio, API gravity, molecular weight, sulfur content, carbon content, hydrogen content, Watson K value, SARA content and paraffin content of single-phase reservoir fluid sample are obtained and are put it into the database.

In another aspect, under high temperature and high pressure, a fluid PVT (pressure volume temperature) test is performed on the obtained single-phase reservoir fluid sample to obtain any one or more of the following fluid properties: bubble point, dew point, CCE test, DL test, CVD test, separator test, density, viscosity, conductivity, compressibility coefficient, FVF, paraffin wax formation condition, asphaltene onset condition, etc. The representative single-phase reservoir fluid sample is subjected to measurements of continuous near-infrared spectrum, NMR, acoustic wave, fluorescence and dielectric constant, etc. under high temperature and high pressure. The measurement results are put into the database.

In another aspect, the continuous near-infrared spectrum, NRM, acoustic wave, fluorescence, dielectric constant and PVT data of a corresponding reservoir fluid sample which are measured during downhole real-time operation include: composition, gas-oil ratio, API gravity, molecular weight, sulfur content, carbon content, hydrogen content, Watson K value, SARA content, paraffin content, bubble point, dew point, CCE, DL, CVD, separator, density, viscosity, conductivity, compressibility coefficient, dielectric constant, paraffin wax formation condition, asphaltene onset condition, etc., which are also put into the database.

In addition, the following data are also put into the database:

a large quantity of result data obtained by CFD and reservoir simulator simulation according to a large number of different reservoir characteristic parameters, different reservoir fluid property parameters and different logging tool geometric parameters;

results obtained by performing the gas-water ratio and ion composition analysis on water samples, and performing measurements of the continuous near-infrared spectrum, NMR, acoustic wave, fluorescence, dielectric constant and pH value under high temperature and high pressure; and results obtained by adding different drilling mud filtrates into the samples and mixing different proportions of gas, oil and water, then performing a PVT test to measure the component composition, API gravity, sulfur content, carbon content, hydrogen content, Watson K value, viscosity, gas-oil ratio, gas-water ratio, ion composition analysis, and performing continuous near-infrared spectrum, NMR, acoustic wave, fluorescence, dielectric constant, pH value, etc. under high temperature and high pressure.

Herein, downhole real-time data and laboratory data are put into the database.

Figure 5:
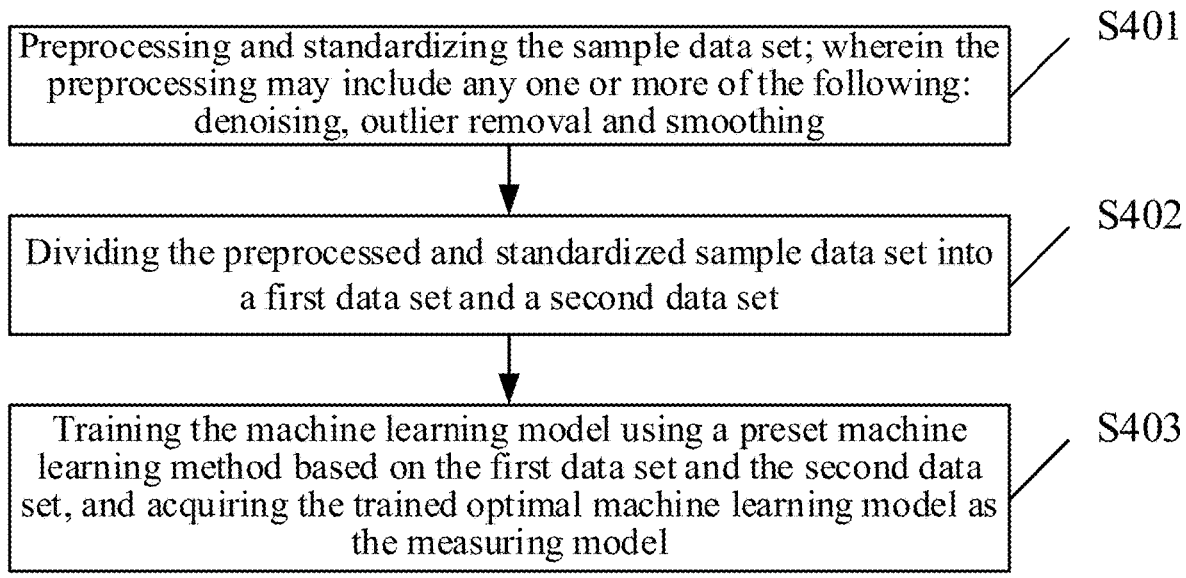
FIG. 5 is a flowchart of a method for extracting a sample data set from a database and training a pre-created machine learning model by the sample data set according to an embodiment of the present application.

In an exemplary embodiment, as shown in FIG. 5, the step of extracting the sample data set from the database, and training the multiple pre-created machine learning models by the sample data set may include steps S401-S403:

S401, preprocessing and standardizing the sample data set, wherein the preprocessing may include any one or more of the following: denoising, outlier removal and smoothing;

In an exemplary embodiment, the database has been established by different methods through the foregoing steps. Before the machine learning, the data set taken out from the database (part or all of the data in the database), that is, the sample data set, may be preprocessed. Original feature vectors/matrices are changed into a more suitable expression for downstream computation. One of the methods may include: firstly, using filters and mathematical methods to perform denoising, outliers removal, smoothing and so on on the data set taken out, and estimate some default values. Then, the data after subjected to the above processing is standardized, for example, to make the data set look like data with standard normal distribution, i.e., Gaussian distribution of zero mean and unit variance.

S402, dividing the preprocessed and standardized sample data set into a first data set and a second data set.

In an exemplary embodiment, the standardized data may be divided into a first data set and a second data set, which may be used for supervised machine learning.

In an exemplary embodiment, the first data set may serve as an input data vector/matrix of the machine learning model, and the second data set may serve as a target data vector/matrix of an output data vector/matrix of the machine learning model.

S403, training the machine learning model using multiple preset machine learning methods based on the first data set and the second data set, and acquiring an optimal trained machine learning model as the measuring model.

In an exemplary embodiment, the preset machine learning method may include a supervised machine learning method.

Figure 6:
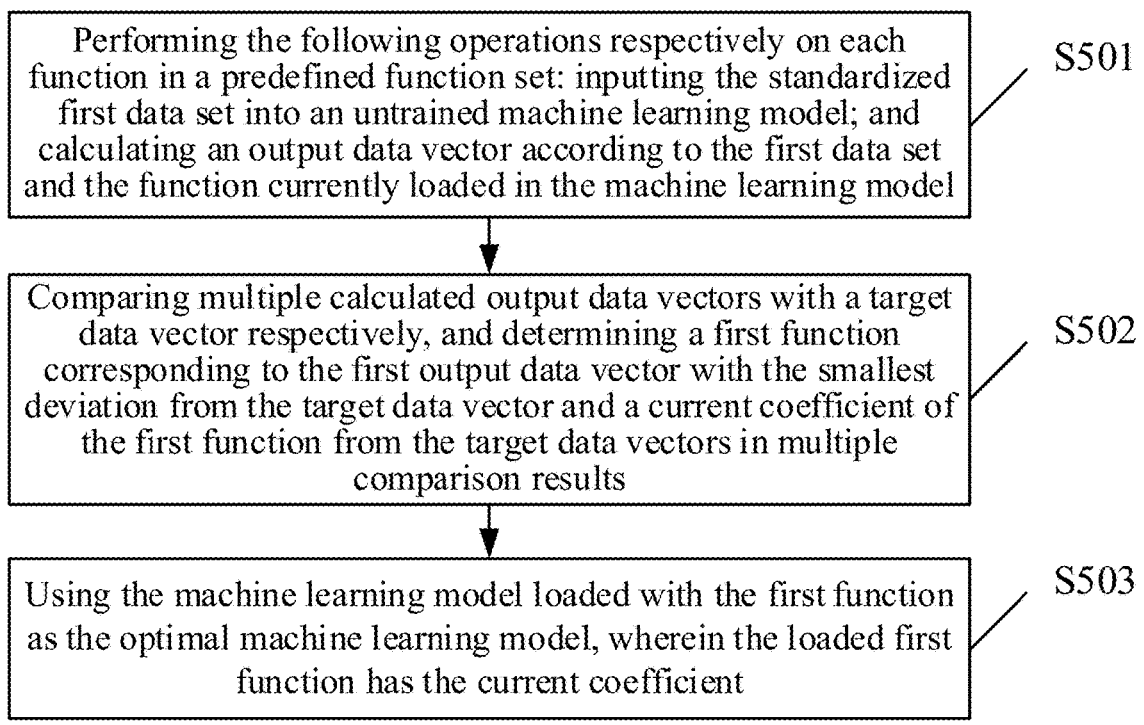
FIG. 6 is a flowchart of a method for training a machine learning model using a preset machine learning method, and obtaining an optimal machine learning model from training results as a measuring model includes according to an embodiment of the present application.

In an exemplary embodiment, as shown in FIG. 6, the step of training the machine learning models using the preset machine learning methods based on the first data set and the second data set, and acquiring the optimal machine learning model from the training results as the measuring model may include steps S501-S503:

S501, performing the following operations respectively on each function in a predefined function set: inputting the standardized first data set into the untrained machine learning models; and calculating the output data vector/matrix according to the first data set and a function currently loaded in the machine learning models;

S502, comparing multiple calculated output data vectors/matrices with a target data vector/matrix respectively, and determining a first function corresponding to the first output data vector/matrix with a smallest deviation from the target data vector/matrix and the current coefficient of the first function from the target data vectors in multiple comparison results; and S503, using the machine learning model loaded with the first function as the optimal machine learning model, wherein the loaded first function has a current coefficient.

In an exemplary embodiment, the supervised machine learning method may include: (1) inputting a standardized input data vector/matrix and a target data vector/matrix; (2) defining a function set; (3) calculating a value of an output data vector/matrix according to the standardized input data vector/matrix and the defined function set, and comparing a calculation result of the function set with a value of the target data vector/matrix taken out from the database to determine whether the function set is good or bad (that is, to determine whether the currently trained machine learning model is good or bad); (4) selecting the optimal function as a result of machine learning (that is, taking the corresponding machine learning model as the measuring model).

Figure 7:
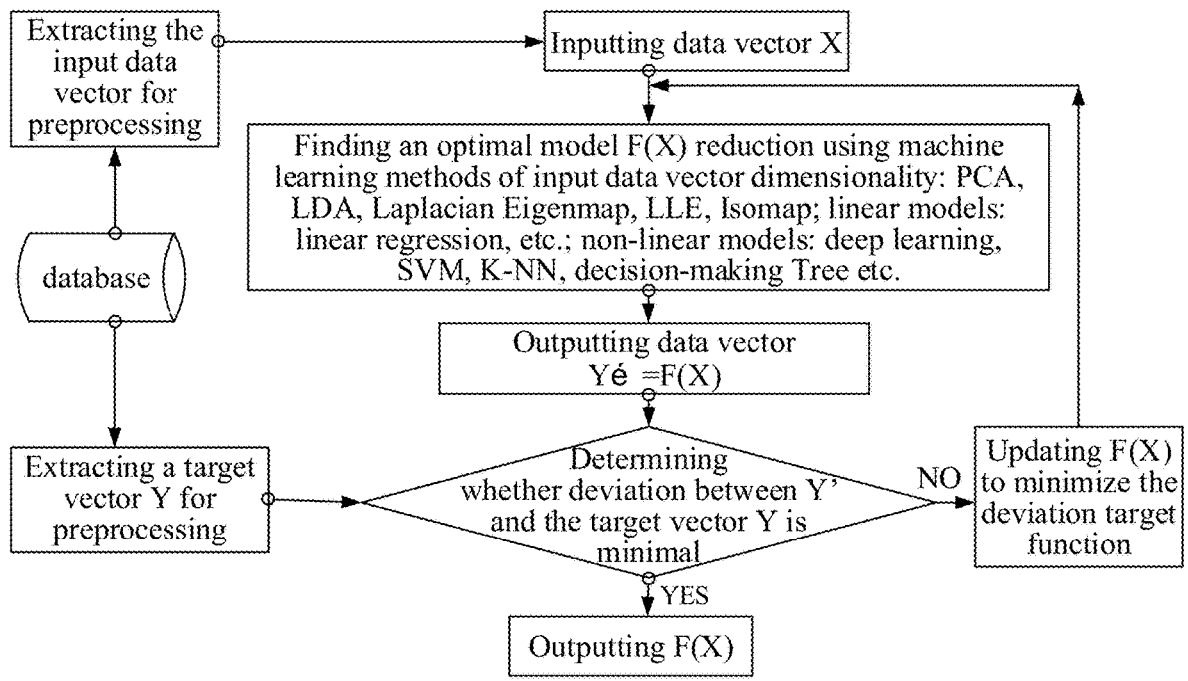
FIG. 7 is a schematic diagram of a supervised machine learning process according to an embodiment of the present application.

As shown in FIG. 7, a schematic flowchart of supervised machine learning according to an exemplary embodiment is given, which includes the following operations:

extracting a related data set from the database for preprocessing and standardization to respectively obtain an input data vector/matrix X and a target vector/matrix Y. X and Y may be reduced by different methods as required. For example, any one or more of the following dimensionality reduction algorithms may be adopted: PCA (Principal Component Analysis), FA (Factor Analysis), ICA (Independent Component Analysis), Independent Component Analysis), NMF (Non-Negative Matrix Factorization), LDA (Linear Discriminant Analysis), Laplacian Eigenmap, LLE (Locally Linear Embedding), Isomap (Isometric Feature Mapping), etc. A function set may be defined, which may be a set of linear functions or a set of nonlinear functions.

For a linear model, an output data vector/matrix value (Y') to be predicted may be expressed as a linear combination of input data vector/matrix (X):

$$Y'=F1(X, W)=XW=w_0+w_1x_1+ \ldots +w_px_p \quad (1)$$

where W is a value of the coefficient (parameter) to be determined.

For a nonlinear model, an output data vector/matrix Y' to be predicted may be expressed as a nonlinear combination of input vector/matrix X:

$$Y'=F2(X, V) \quad (2)$$

where V is a value of the coefficient (parameter) to be determined.

For the linear model, the parameters (W) of the linear model may be regressed by using Ordinary Least Squares, Ridge Regression, Bayesian regression, Bayesian Ridge Regression, Logistic Regression, Random Gradient Descent Method, Perceptron Method, Polynomial Regression, PLS (Partial Least Squares) and other algorithms.

In an exemplary embodiment, for the nonlinear model, algorithms such as SVM (Support Vector Machines), Deep Learning, Multilayer Neural Network, K-Nearest Neighbor Algorithm, Gaussian Processes Regression, Bayesian Regression, Decision Tree, and Random Forests may be adopted. After each output data vector/matrix Y' is obtained, whether a deviation between the output data vector/matrix Y' and the target vector/matrix Y is the smallest is determined. If the deviation is the smallest, F(X) is output, if not, F(X) is updated to minimize the deviation target function, and then return to the step of dimensionality reduction. The purpose of these machine learning methods is to find a set of optimal V coefficient (parameter) values to minimize the deviation between the predicted output data vector/matrix Y' and the target vector/matrix Y retrieved from the database. Generally, the deviation objective function is: $\min\|Y-Y'\|$.

In an exemplary embodiment, the data extracted from the database may be divided into two groups in the process of machine learning: one is a training data set, and the other is a test data set. The training data set may be used for determine an optimal function (such as the aforementioned first function) and coefficients (parameters) of the optimal function. The test data set may be used for cross-validation to ensure that the obtained optimal function and the coefficients (parameters) of the optimal function will not lose the original accuracy (i.e., over-fitting phenomenon does not occur) when they are used for measuring the formation fluid composition and property prediction. Usually, functions that are too simple may hardly guarantee the prediction accuracy, while functions that are too complex may cause the over-fitting phenomenon. Therefore, a Gaussian Processes may be used for optimizing the parameters.

In an exemplary embodiment, after the optimal machine learning model is obtained from the above steps, the measuring model used may be determined to complete the creation and training of the measuring model.

In an exemplary embodiment, the downhole hydrocarbon formation tester may be a downhole midway hydrocarbon formation tester.

In an exemplary embodiment, before the step of using the signal measured by the sensor on the downhole hydrocarbon formation tester in real-time as the input data of the measuring model and inputting the input data into the measuring model, the method further includes:

loading the pre-trained measuring model into a downhole hydrocarbon formation tester to input a signal measured by a sensor on a downhole hydrocarbon formation tester in real-time into the measuring model during the real-time logging process of the downhole hydrocarbon formation tester.

In an exemplary embodiment, in combination with the above-mentioned database and measuring model, there are two methods for measuring a composition and a property of a reservoir fluid during downhole wireline formation testing and hydrocarbon formation testing while drilling: the first method is an off-line mode, and the other method is an on-line mode.

Figure 8:
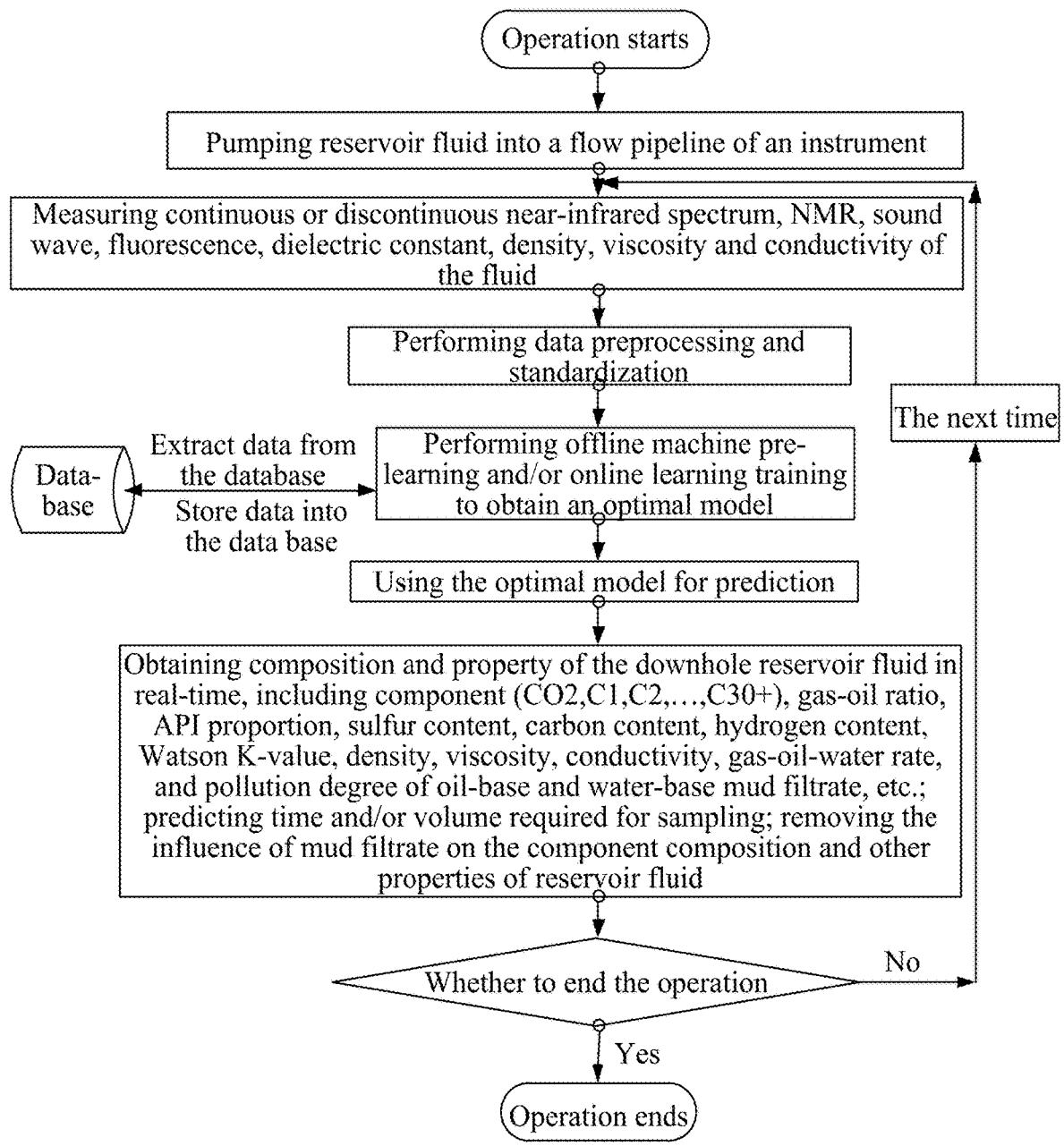
FIG. 8 is a schematic diagram of application of downhole wireline formation testing and hydrocarbon formation testing while drilling based on database and measuring model according to an embodiment of the present application.

In an exemplary embodiment, in the off-line mode, related data may be retrieved from the database, and the related model may be trained by the aforementioned machine learning method to obtain functions and parameters of the related model, thereby obtaining the final trained measuring model. Therefore, the obtained measuring model may be embedded into equipment and/or software for downhole wireline formation testing and hydrocarbon formation testing while drilling, and may be applied in real-time during downhole wireline formation testing and hydrocarbon formation testing while drilling. The flowchart during application is shown in FIG. 8, including:

pumping reservoir fluid into a flow pipeline of an instrument after operation starts;

measuring continuous or discontinuous near-infrared spectrum, NMR, sound wave, fluorescence, dielectric constant, density, viscosity and conductivity of the fluid;

performing data preprocessing and standardization;

performing offline machine pre-learning and/or online learning training to get an optimal model, in which data may be retrieved from the database and stored in the database;

using the optimal model for prediction.

obtaining composition and properties of the downhole reservoir fluid in real-time, including component (CO2,C1, C2, ..., C30+), gas-oil ratio, API gravity, sulfur content, carbon content, hydrogen content, Watson K value, density, viscosity, conductivity, gas-oil-water rate, and contamination degree of oil-based and water-based mud filtrates, etc.; predicting time and/or volume required for sampling; removing influence of mud filtrate on the composition and other properties of the reservoir fluid; and determining whether to end the operation; if yes, the operation is ended; if not, continue to perform from the step of measuring continuous or non-continuous near-infrared spectrum, NMR, acoustic wave, fluorescence, dielectric constant, density, viscosity and conductivity of the fluid at the next time.

In an exemplary embodiment, the downhole wireline and hydrocarbon formation tester while drilling is put into the well to a required depth, the probe and/or packer are in contact with the reservoir and sealed, and the reservoir fluid is pumped into the flow pipeline of the tester. The fluid flows through various sensors on the tester (such as one or more of the following: density, viscosity, conductivity, dielectric constant, continuous near-infrared spectrum, discontinuous near-infrared spectrum, nuclear magnetic, acoustic wave, fluorescence, dielectric constant sensors, etc.) These sensors may measure the properties of flowing fluid in real-time (such as one or more of the following: density, viscosity, conductivity, dielectric constant, continuous near-infrared spectrum, discontinuous near-infrared spectrum, nuclear magnetic, acoustic wave, fluorescence, etc.). These measured fluid properties may be preprocessed and standardized by the preprocessing and standardization method mentioned above, which may be used as the input of the measuring model trained by the machine learning method mentioned above. The measuring model may be used for interpretation and prediction, and the composition of downhole reservoir fluid may be obtained in real-time: including CO2, C1, C2, ..., C5, C6+, or CO2, C1, C2, ..., C6, C7+, or CO2, C1, C2, ..., C7, C8+, ..., or CO2 C1, C2, ..., C29, C30+. The property of downhole reservoir fluid may also be obtained in real-time: gas-oil ratio, API gravity, molecular weight, density, viscosity, conductivity, gas-oil-water ratio, sulfur content, carbon content, hydrogen content, Watson K value, SARA (saturated hydrocarbon, aromatic hydrocarbon, resin, asphaltene) content, paraffin content, sound speed, bubble point, dew point, CCE, DL, CVD, separator test, compressibility coefficient, formation volume factor of reservoir fluid, paraffin wax formation condition, asphaltene onset condition, and contamination degree of oil-based and water-based mud filtrates, etc. Because at the same depth, not only will the downhole real-time measurement be performed, but also samples will be taken and sent to the laboratory for PVT measurement. After passing strict quality inspection, these measured data may be added to the database to enrich the database continuously. In addition, the model and parameters of machine learning may be updated regularly or irregularly to obtain better results of downhole measurement.

In an exemplary embodiment, the on-line mode may be divided into two types. The first mode is to extract the related data from the database, train the related model by the aforementioned machine learning method, to obtain the parameters of the related model (i.e., the measuring model is obtained). Related model and parameters (the measuring model) may be embedded into the equipment and/or software for downhole wireline formation testing and hydrocarbon formation testing while drilling. The parameters of the measuring model are adjusted and optimized by using the data measured during the downhole wireline formation testing and hydrocarbon formation testing while drilling (especially time series data measured in real-time, and the real-time data may also be stored in the database), and the obtained related model and parameters (optimized measuring model) are used for making predictions. The second mode is to directly use the data measured during the downhole wireline formation testing and hydrocarbon formation testing while drilling (especially the time series data measured in real-time, and the real-time data may also be stored in the database) as the input data, and train the related model and parameters with the aforementioned machine learning method. Then, the related model and parameters (the measuring model) are used for prediction.

In an exemplary embodiment, the on-line mode may be applied to real-time prediction. For example, the time and/or volume required for sampling, the contamination degree of mud filtrate, and the removal of influence of mud filtrate contamination on composition and other properties (such as one or more of the following: bubble point, dew point, density, viscosity, conductivity, dielectric constant, continuous near-infrared spectrum, discontinuous near-infrared spectrum, nuclear magnetic resonance, acoustic wave, fluorescence, dielectric constant, gas-oil ratio, API gravity, molecular weight, sulfur content, carbon content, hydrogen content, Watson K value, oil-water rate, SARA content, paraffin content, compressibility coefficient, formation volume factor of reservoir fluid, paraffin wax formation condition, asphaltene onset condition) of reservoir fluid are predicted.

In an exemplary embodiment, the method may further include supplementing an output data vector/matrix whose deviation with respect to the target data vector/matrix meets a preset deviation threshold to the database in one or more of the following processes: during the training process of the machine learning model and the implementation process of measuring the composition and the properties of the formation fluid.

Figure 9:
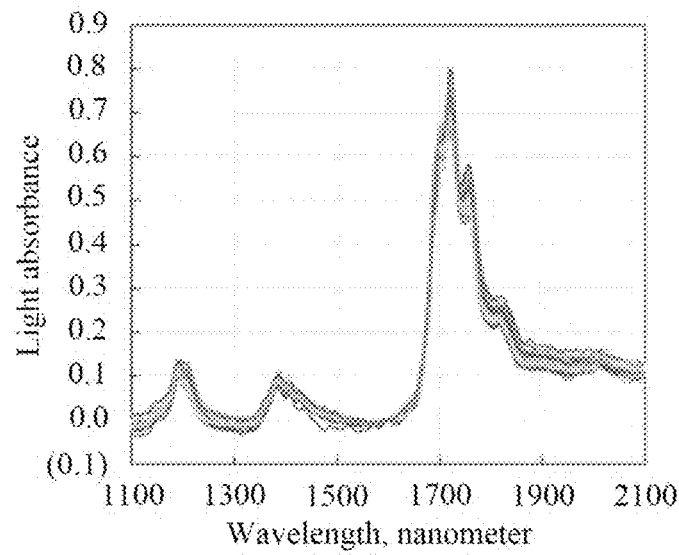
FIG. 9(a) is a schematic diagram of spectra of some fluids (light oil+gas) taken out from a database according to an embodiment of the present application.
FIG. 9(b) is a schematic diagram of spectra of some fluids (various crude oil) taken out from a database according to an embodiment of the present application.
Figure 9:
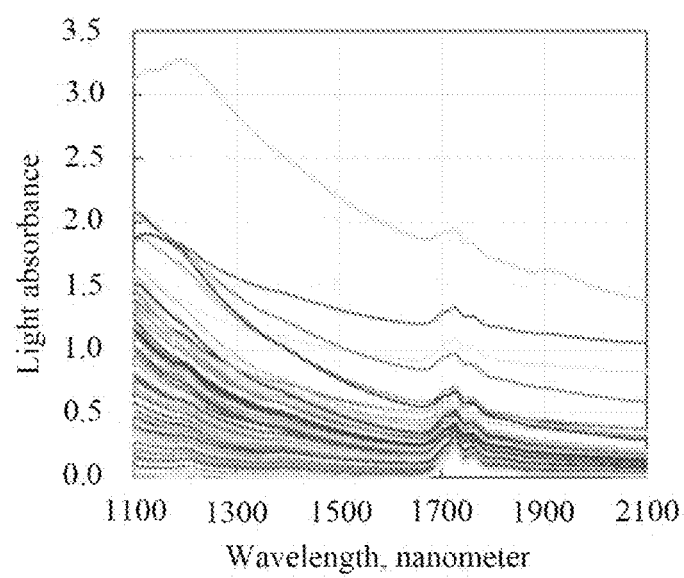

In an exemplary embodiment, a large number of reservoir fluid samples (dry gas, wet gas, condensate gas, volatile oil, black oil and heavy oil) may be collected in advance, and a large quantity of tested data is measured on these reservoir fluid samples to establish an in-house database. Continuous or discontinuous near-infrared spectrums, component compositions up to C30+, gas-oil ratios, API gravities, fluid formation volume factor, density and viscosity data of various reservoir fluids may be extracted from this database. The spectral data of some fluids are shown in FIGS. 9(a) and 9(b).

Figure 10:
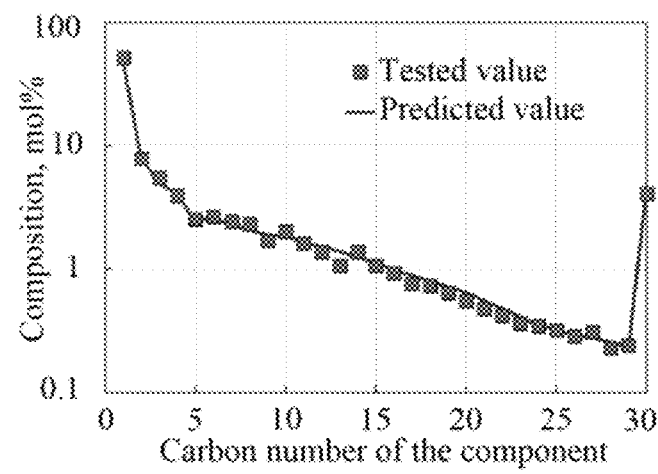
FIG. 10 is a schematic diagram of comparison between compositions of reservoir fluids up to C30+ component predicted by a measuring model and tested values according to an embodiment of the present application.

In this embodiment, these data may be preprocessed and standardized. Near-infrared spectrum is used as an input data vector/matrix, while other properties are used as a target data vector/matrix. The processed data vector/matrix is put into an in-house machine learner, and these data are trained by supervised machine learning and are cross-validation. The optimal model and parameters (that is, the final measuring model) are used for prediction. That is, the near-infrared spectrum is used as the input data vector/matrix, and the obtained machine learning model (i.e., the measuring model) is used for predicting the fluid properties. The prediction results are as follows:

FIG. 10 shows comparison between the compositions of C30+ components predicted by a machine learning model (here referred to as the measuring model) and tested values, and the results predicted by the machine learning model are consistent with the tested values. The heavy components in the reservoir fluid may also be combined together to obtain the compositions of C6+, C7+, . . . , C29+ and other components, that is, $Z_{Cn+} = \Sigma_{i=n}^{C30+} Z_{Ci}$; in which ZCn+ and ZCi are the compositions of Cn+ and Ci.

Figure 11:
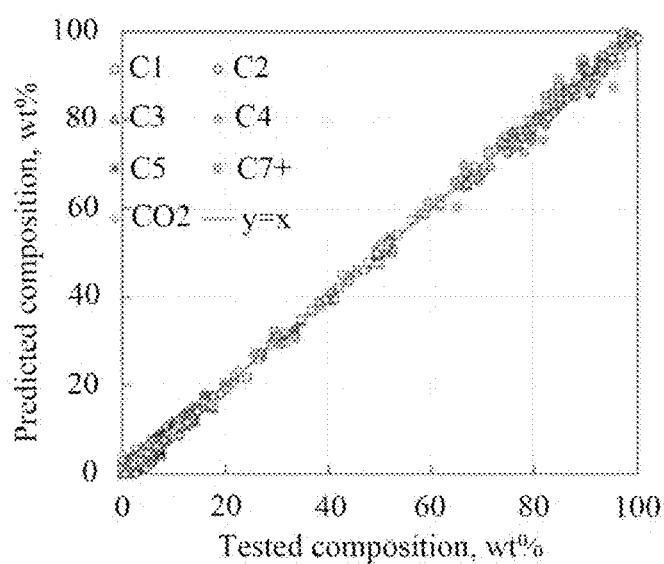
FIG. 11(a) is a schematic diagram of comparison between compositions of reservoir fluids predicted by a measuring model and tested values according to an embodiment of the present application.
FIG. 11(b) is a schematic diagram of comparison between gas-oil ratios of reservoir fluids predicted by a measuring model and tested values according to an embodiment of the present application.
Figure 11:
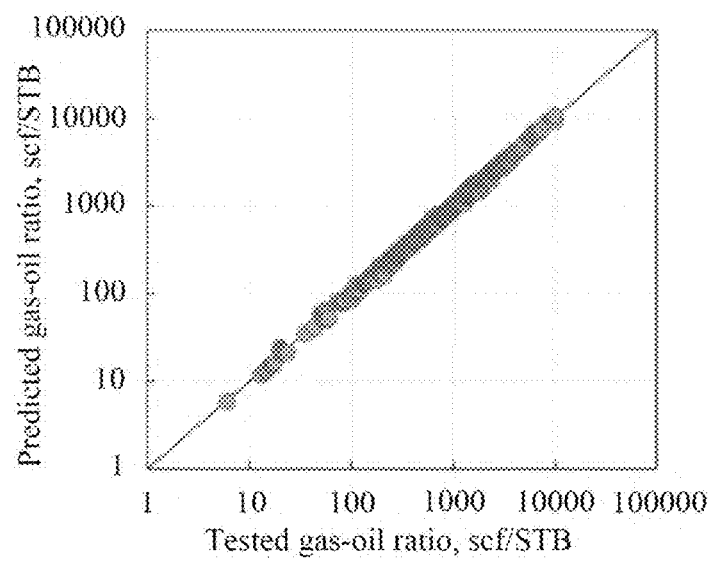

In FIG. 11(a) and FIG. 11(b), the components (CO2, C1, C2, C3, C4, C5, C7+) and the gas-oil ratios predicted by the machine learning model (here referred to as the measuring model) are compared with the test values. The use of a 256-channel near-infrared spectrometer and machine learning method has more information and features than other existing downhole spectrometers, therefore more accurate prediction results of component compositions and gas-oil ratios can be obtained.

Figure 12:
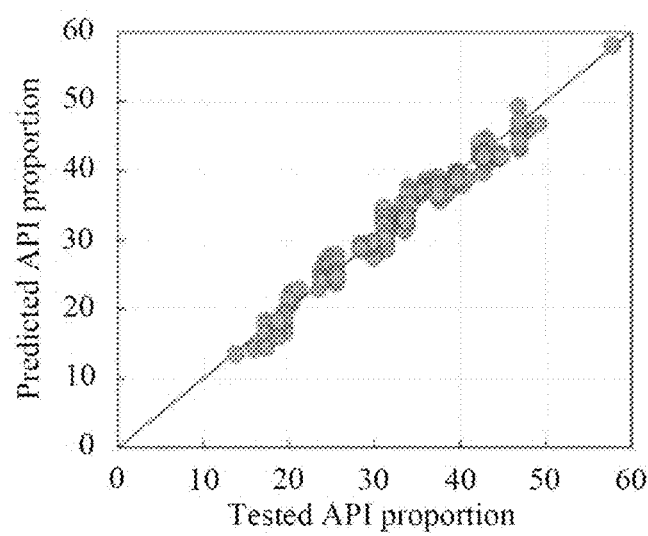
FIG. 12(a) is a schematic diagram of comparison between API gravities of reservoir fluids predicted by a measuring model and the tested value according to an embodiment of the present application.
FIG. 12(b) is a schematic diagram of the comparison between formation volume factors of reservoir fluids predicted by a measuring model and tested values according to an embodiment of the present application.
Figure 12:
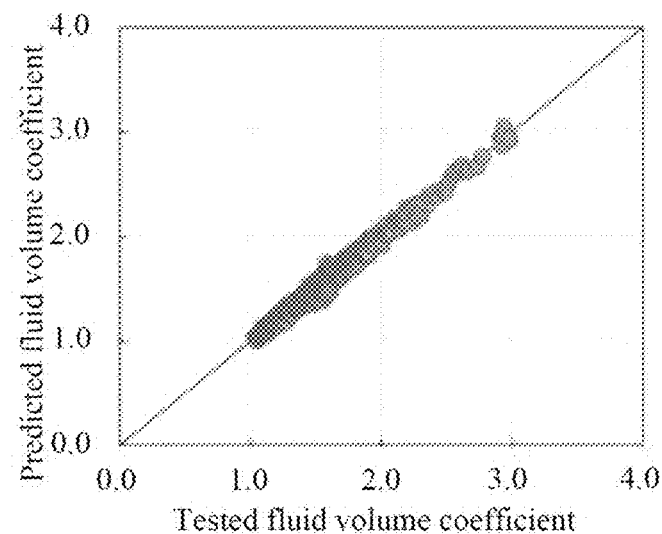
Figure 13:
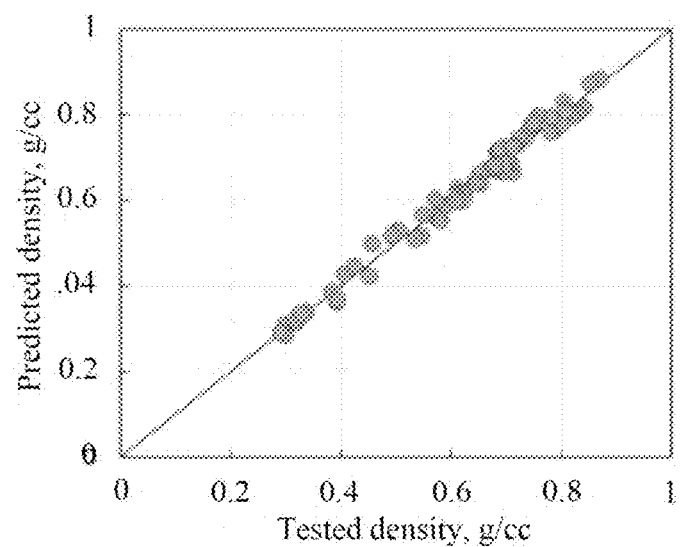
FIG. 13(a) is a schematic diagram of comparison between densities of reservoir fluids predicted by a measuring model and tested values according to an embodiment of the present application.
FIG. 13(b) is a schematic diagram of comparison between viscosities of reservoir fluids predicted by a measuring model and tested values according to an embodiment of the present application.
Figure 13:
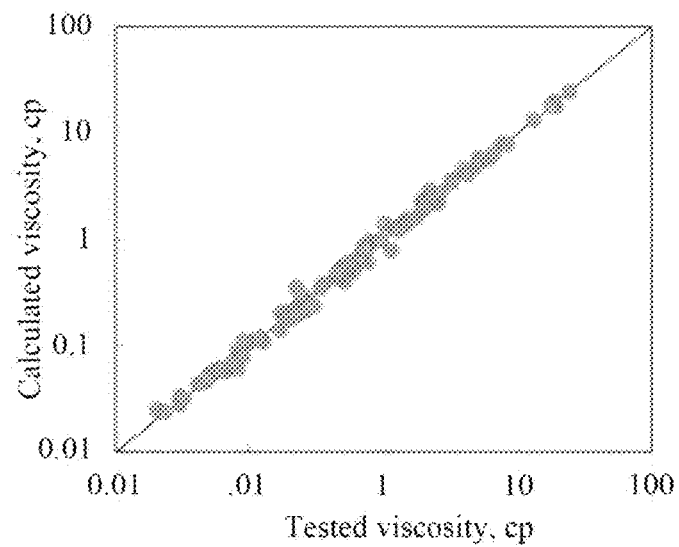

In FIG. 12(a) and FIG. 12(b), the API gravity and fluid formation volume factor predicted by the machine learning model (here referred to as the measuring model) are compared with the tested values. FIG. 13(a) and FIG. 13(b) show the comparison between reservoir fluid densities and viscosities predicted by machine learning model and tested values. It may be seen from these comparison charts that the machine learning model has relatively good learning and prediction capability.

In an exemplary embodiment, with the continuous improvement and enrichment of the database, the machine learning model (here referred to as the measuring model) may be continuously updated and improved. Besides supervised machine learning methods, in-house machine learners may also include semi-supervised machine learning methods and unsupervised machine learning methods. A more intelligent AI (Artificial Intelligence) product for downhole wireline formation testing and hydrocarbon formation testing while drilling may be obtained through combination of the database and these machine learning methods.

Figure 14:
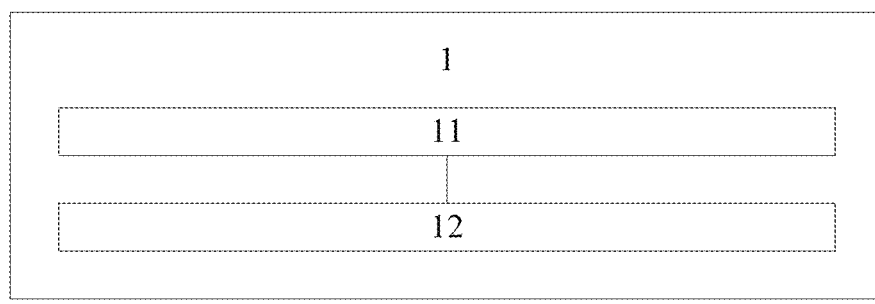
FIG. 14 is a schematic diagram showing components of a system for measuring a composition and a property of a formation fluid according to an embodiment of the present application.

An embodiment of the present application further provides a system 1 for measuring a composition and a property of a formation fluid. As shown in FIG. 14, the system may include: a processor 11 and a computer readable storage medium 12, wherein instructions are stored in the computer readable storage medium 12, and the processor 11 is configured to execute the instructions to perform the following operations:

acquiring a measuring model used for measuring a composition and a property of a formation fluid;

using a signal measured by a sensor on a downhole hydrocarbon formation tester in real-time as input data and inputting the input data into the measuring model;

processing the input data by the measuring model; and directly outputting a processing result as data on the composition and the property of the real-time formation fluid, or parsing the data on the composition and the property of the real-time formation fluid according to the processing result.

In an exemplary embodiment, the method for measuring composition and property of formation fluid described in any of the above embodiments may be performed when the processor 11 executes the instructions.

Although the embodiments disclosed in the present application are as above, the contents described are only for the convenience of understanding of the embodiments adopted in the present application, and is not intended to limit the embodiments of the present application. Without departing from the essence and scope disclosed in the present application, any person skilled in the art of the embodiments of the present application can make any modifications and changes in the implementation form and details, but the scope of patent protection of the present application shall still be subject to the scope defined in the appended claims.

What is claimed is:

1. A method for measuring composition and property of formation fluid, comprising:
   acquiring a measuring model used for measuring a composition and a property of a formation fluid;
   using a signal measured by a sensor on a downhole hydrocarbon formation tester in real-time as input data and inputting the input data into the measuring model;
   processing the input data by the measuring model; and
   directly outputting a processing result as data on the composition and the property of the real-time formation fluid, or parsing the data on the composition and the property of the real-time formation fluid according to the processing result;
   wherein acquiring the measuring model used for measuring the composition and the property of the formation fluid comprises retrieving a pre-created and pre-trained measuring model, or creating and training the measuring model in real-time.

2. The method for measuring composition and property of formation fluid according to claim 1, wherein before using the signal measured by the sensor on the downhole hydrocarbon formation tester in real-time as the input data of the measuring model and inputting the input data into the measuring model, the method further comprises:
   loading the pre-trained measuring model into the downhole hydrocarbon formation tester to input the signal measured by the sensor on the downhole hydrocarbon formation tester in real-time into the measuring model during a real-time logging process of the downhole hydrocarbon formation tester.

3. The method for measuring composition and property of formation fluid according to claim 2, wherein creating and training the measuring model comprises:
   establishing a database about compositions and properties of various reservoir fluids and measurement signals of downhole sensors;
   extracting a sample data set from the database, and training pre-created machine learning models by the sample data set; and
   acquiring an optimal machine learning model from trained machine learning models as the measuring model.

4. The method for measuring composition and property of formation fluid according to claim 3, wherein establishing the database about the compositions and the properties of the various reservoir fluids and the measurement signals of the downhole sensors comprises:
  acquiring single-phase reservoir fluid samples meeting a preset requirement in one or more of following manners: surface sampling and downhole sampling; the single-phase reservoir fluid samples comprise oil phase reservoir fluid sample, gas phase reservoir fluid sample and water phase reservoir fluid sample;
  performing single-stage flash on the single-phase reservoir fluid sample at standard atmospheric pressure and room temperature to separate equilibrium flashed gas and liquid;
  performing gas chromatography analysis on the flashed gas and the flashed liquid respectively to obtain a composition and a first property of the single-phase reservoir fluid sample by use of mass balance calculations; performing a fluid pressure volume temperature (PVT) test on the single-phase reservoir fluid sample under a first preset pressure and a first preset temperature to obtain a second property of the single-phase reservoir fluid sample; wherein the first preset pressure is greater than the standard atmospheric pressure and the first preset temperature is greater than the room temperature; and
  adding data related to the composition, the first property and the second property of the single-phase reservoir fluid sample as a part of big data of the formation fluid into the database.

5. The method for measuring composition and property of formation fluid according to claim 2,
  wherein the first property comprises any one or more of the following: gas-oil ratio, American Petroleum Institute (API) gravity, molecular weight, sulfur content, carbon content, hydrogen content, Watson K value, SARA content and paraffin content; wherein SARA refers to saturated hydrocarbon, aromatic hydrocarbon, resin and asphaltene; and
  the second property comprises any one or more of the following: bubble point, dew point, constant composition expansion (CCE) test characteristics, differential liberation (DL) test characteristics, constant volume depletion (CVD) test characteristics, separator test characteristics, density, viscosity, conductivity, compressibility coefficient, formation volume factor, paraffin wax formation condition and asphaltene onset condition.

6. The method for measuring composition and property of formation fluid according to claim 5, wherein the measuring model is obtained by training pre-created machine learning models based on big data about compositions and properties of various reservoir fluids and measurement signals of downhole sensors as sample data sets.

7. The method for measuring composition and property of formation fluid according to claim 4, further comprising:
  performing of any one or more of the following:
  measuring volume, temperature and pressure of the flashed gas when the gas chromatography analysis is performed on the flashed gas and adding the volume, the temperature and the pressure of the flashed gas into the database;
  measuring volume, temperature, pressure, density and molecular weight of the flashed liquid when the gas chromatography analysis is performed on the flashed liquid and adding the volume, the temperature, the pressure, the density and the molecular weight of the flashed liquid into the database;
  performing any one or more of the following measurements on the single-phase reservoir fluid sample under the first preset pressure and the first preset temperature: continuous near-infrared spectrum, nuclear magnetic resonance (NMR), acoustic wave, fluorescence and dielectric constant measurements, and results of the measurements are added into the database.

8. The method for measuring composition and property of formation fluid according to claim 7, wherein the measuring model is obtained by training pre-created machine learning models based on big data about compositions and properties of various reservoir fluids and measurement signals of downhole sensors as sample data sets.

9. The method for measuring composition and property of formation fluid according to claim 4, further comprising adding different drilling mud filtrates into different single-phase reservoir fluid samples, and performing the PVT test on the single-phase reservoir fluid samples in which corresponding drilling mud filtrates are added.

10. The method for measuring composition and property of formation fluid according to claim 4 wherein the measuring model is obtained by training pre-created machine learning models based on big data about compositions and properties of various reservoir fluids and measurement signals of downhole sensors as sample data sets.

11. The method for measuring composition and property of formation fluid according to claim 3, wherein extracting the sample data set from the database, and training the pre-created machine learning models by the sample data set comprises:
  preprocessing and standardizing the sample data set, wherein the preprocessing comprises any one or more of the following: denoising, outlier removal and smoothing;
  dividing the preprocessed and standardized sample data set into a first data set and a second data set;
  training each of the machine learning models using a preset machine learning method based on the first data set and the second data set, and obtaining an optimal trained machine learning model among all the trained models as the measuring model;
  wherein the first data set serves as an input data vector/matrix of the machine learning model, and the second data set serves as a target data vector/matrix of an output data vector/matrix of the machine learning model.

12. The method for measuring composition and property of formation fluid according to claim 11, wherein the preset machine learning method comprises a supervised machine learning method;
  training each of the machine learning models using the preset machine learning method based on the first data set and the second data set, and obtaining the optimal trained machine learning model among all the trained models as the measuring model comprises:
  performing following operations respectively on each function in a predefined function set: inputting a standardized first data set into each untrained machine learning model; calculating the output data vector/matrix according to the first data set and a function currently loaded in the machine learning model;
  comparing a plurality of calculated output data vectors/matrices with the target data vector/matrix respectively, and determining a first function corresponding to the first output data vector/matrix with the smallest deviation with respect to the target data vector/matrix and a current coefficient of the first function from target data vectors/matrix in a plurality of comparison results; and using a machine learning model loaded with the first function as an optimal trained machine learning model, wherein the loaded first function has the current coefficient.

13. The method for measuring composition and property of formation fluid according to claim 12, further comprising supplementing an output data vector/matrix whose deviation with respect to the target data vector/matrix meets a preset deviation threshold to the database in one or more of following processes:

during a training process of the machine learning models and an implementation process of measuring the composition and the property of the formation fluid.

14. The method for measuring composition and property of formation fluid according to claim 3, wherein the measuring model is obtained by training pre-created machine learning models based on big data about compositions and properties of various reservoir fluids and measurement signals of downhole sensors as sample data sets.

15. The method for measuring composition and property of formation fluid according to claim 2, wherein the measuring model is obtained by training pre-created machine learning models based on big data about compositions and properties of various reservoir fluids and measurement signals of downhole sensors as sample data sets.

16. The method for measuring composition and property of formation fluid according to claim 1, wherein the measuring model is obtained by training pre-created machine learning models based on big data about compositions and properties of various reservoir fluids and measurement signals of downhole sensors as sample data sets.

17. A system for measuring composition and property of formation fluid, comprising: a processor and a computer readable storage medium, wherein instructions are stored in the computer readable storage medium, and the processor is configured to execute the instructions to perform the method for measuring composition and property of formation fluid according to claim 1.

\* \* \* \* \*